(12) United States Patent
Schreivogel

(10) Patent No.: US 10,914,702 B2
(45) Date of Patent: Feb. 9, 2021

(54) GAS SENSOR AND METHOD FOR DETECTING A GAS

(71) Applicant: Robert Bosch GmbH, Stuttgart (DE)

(72) Inventor: Martin Schreivogel, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 54 days.

(21) Appl. No.: 16/343,077

(22) PCT Filed: Nov. 23, 2016

(86) PCT No.: PCT/EP2016/078593
§ 371 (c)(1),
(2) Date: Apr. 18, 2019

(87) PCT Pub. No.: WO2018/095524
PCT Pub. Date: May 31, 2018

(65) Prior Publication Data
US 2020/0049649 A1    Feb. 13, 2020

(51) Int. Cl.
*G01N 27/22* (2006.01)
*G01N 33/00* (2006.01)

(52) U.S. Cl.
CPC ....... *G01N 27/221* (2013.01); *G01N 33/0027* (2013.01); *G01N 2027/222* (2013.01)

(58) Field of Classification Search
None
See application file for complete search history.

(56) References Cited

U.S. PATENT DOCUMENTS

| 5,018,380 A * | 5/1991 | Zupancic | G01N 27/227 73/23.2 |
| 5,595,647 A * | 1/1997 | Hoetzel | G01N 27/407 204/424 |
| 9,164,052 B1 | 10/2015 | Speer et al. | |
| 2009/0159447 A1* | 6/2009 | Cui | G01N 27/125 204/431 |
| 2014/0290339 A1* | 10/2014 | Kunz | G01N 27/227 73/31.06 |

FOREIGN PATENT DOCUMENTS

| DE | 19642453 A1 | 4/1998 |
| DE | 19710358 A1 | 9/1998 |
| DE | 10210819 A1 | 10/2003 |
| DE | 102004034192 A1 | 2/2006 |
| DE | 102004041620 A1 | 3/2006 |
| DE | 102013205540 A1 | 10/2014 |
| DE | 102014200481 A1 | 7/2015 |

OTHER PUBLICATIONS

International Search Report for PCT/EP2017/078593, dated Mar. 15, 2017.

* cited by examiner

*Primary Examiner* — Jas A Sanghera
(74) *Attorney, Agent, or Firm* — Norton Rose Fulbright US LLP; Gerard Messina

(57) ABSTRACT

A gas sensor combines two separate measurement methods in one shared structure. By way of the gas sensor, a qualitative or quantitative measurement of gases based on measurement of a variation in electrical conductivity, and a measurement of a change in work function based on a variation in the capacitance or impedance between two electrodes, can be carried out.

10 Claims, 2 Drawing Sheets

GAS SENSOR AND METHOD FOR DETECTING A GAS

FIELD

The present invention relates to a gas sensor and to a method for detecting a gas.

BACKGROUND INFORMATION

Gas sensors are used in numerous application sectors. In particular, various types of microstructured gas sensors are used. For example, microstructured gas sensors that ascertain, by way of a resistive structure, a change in the conductivity of a gas-sensitive material between two electrodes can be used. In addition, sensors in which a change in work function is detected are also known.

German Patent Application No. DE 10 2013 205 540 A1 describes a sensor element for qualitative and quantitative detection of a gas. Detection of the gas is based on measuring a change in the work function of a gas-sensitive material with the aid of a metal-insulator-metal structure.

Composites or organic compounds are increasingly being used as gas-sensitive materials. Novel sensor materials can in some cases also react sensitively to several different gases, and both the work function and the conductivity of the gas-sensitive material can change. A detailed understanding of the signal-creation process of such gas-sensitive materials in most cases does not exist.

SUMMARY

The present invention relates to a gas sensor, and a method for detecting a gas.

In accordance with the present invention, the following is provided:

An example gas sensor, having an electrically conductive back electrode, a front electrode, a dielectric layer, and a gas-sensitive layer. The front electrode encompasses two electrode elements electrically separated from one another. The dielectric layer is disposed between the back electrode and the front electrode. The gas-sensitive layer is disposed on a side of the dielectric layer on which the front electrode is also disposed.

The following is furthermore provided:

An example method for detecting a gas using the gas sensor according to the present invention. The method encompasses the steps of: ascertaining an electrical conductivity between the two electrode elements of the front electrode; and ascertaining an impedance and/or a capacitance between the back electrode and the two electrode elements of the front electrode. The method furthermore encompasses a step for identifying a gas based on a comparison of the ascertained electrical conductivity between the two electrode elements of the front electrode, and of the ascertained impedance or ascertained capacitance between the back electrode and the two electrode elements of the front electrode, with predetermined values.

The present invention is based on the recognition that gas sensors whose detection principle is based only on ascertaining an electrical conductivity, or alternatively only on determining the change in a work function from a gas-sensitive substance, in many cases do not enable unequivocal detection of a substance.

The present invention is therefore takes that recognition into account and provides a capability with which the reliability with which a gas is detected can be increased by combining several detection principles in one gas sensor.

The present invention provides for that purpose a gas sensor that has both structures for gas-sensitive detection of an electrical conductivity and structures for detecting a gas-sensitive change in an impedance or a capacitance so that a variation in work function can be determined on the basis thereof.

Reliability in the detection of individual substances, in particular different gases, can be increased thanks to the combination of both measurement principles in a single gas sensor. By integrating two measurement principles into a single gas sensor it is possible to create a particularly efficient sensor structure that requires less physical space as compared with multiple individual gas sensors.

The selectivity of the gas sensor can thus be enhanced by evaluating the information relating to electrical conductivity and to the impedance or capacitance that corresponds to the work function. A cross-sensitivity to moisture due to leakage current paths can furthermore be eliminated.

Advantageous embodiments and refinements are described herein with reference to the Figures.

In an embodiment of the present invention, the gas-sensitive layer encompasses a phthalocyanine, a metal oxide, and/or a carbonate. The gas-sensitive layer can encompass in particular, for example, zinc oxide (ZnO), tin oxide ($SnO_2$), chromium oxide ($Cr_2O_3$), manganese oxide ($Mn_2O_3$), cobalt oxide ($Co_3O_4$), nickel oxide (NiO), copper oxide (CuO), strontium oxide (SrO), indium oxide ($In_2O_3$), tungsten oxide ($WO_3$), titanium oxide ($TiO_2$), vanadium oxide ($V_2O_3$), iron oxide ($Fe_2O_3$), germanium oxide ($GeO_2$), niobium oxide ($Nb_2O_3$), molybdenum oxide ($MoO_3$), tantalum oxide ($Ta_2O_5$), lanthanum oxide ($La_2O_3$), cerium oxide ($CeO_2$), neodymium oxide ($Nd_2O_3$), or mixtures thereof, as well as composite materials made up of a conductive electrode and, for example, carbonates such as barium carbonate.

According to a further embodiment of the present invention, the dielectric layer encompasses a ferroelectric. The dielectric layer here is, in particular, a polarizable thin layer. For example, the dielectric layer is polarizable in such a way that the dielectric layer has a relative permittivity that is lower, by a factor in the range of more than or equal to 1.1, in the polarized state than in a non-polarized state. The thickness of the dielectric layer is preferably less than or equal to 10 μm. In particular, the dielectric layer can be less than or equal to 1 μm, 500 nm, or 200 nm.

According to a further embodiment of the present invention, the gas-sensitive layer encompasses a porous structure and/or cavities. A gas-sensitive layer of this kind having a porous structure and/or having cavities makes it possible for the gas that is to be detected to influence the dielectric layer particularly effectively.

According to a further embodiment of the present invention, the back electrode of the gas sensor is disposed on a carrier substrate. In particular, the carrier substrate can also encompass a heating element or further functional elements.

According to a further embodiment of the present invention, the front electrode encompasses an interdigital electrode. Interdigital electrodes of this kind are particularly suitable, as a result of their structure, for detecting an electrical conductivity.

According to a further embodiment of the present invention, the gas sensor encompasses an evaluation device. The evaluation device is electronically coupled to the back electrode and to the two electrode elements of the front electrode. The evaluation device is designed to ascertain an electrical conductivity between the two electrode elements of the front electrode. The evaluation device is furthermore designed to ascertain an impedance and/or a capacitance between the back electrode and the two electrode elements of the front electrode.

According to a further embodiment of the present invention, the evaluation device is designed to connect the electrode elements of the front electrode electrically to one another when the impedance and/or capacitance between the back electrode and the two electrode elements of the front electrode is being ascertained. The two electrode elements of the front electrode can thereby serve together as one electrode, while the back electrode constitutes the other electrode upon determination of the capacitance or impedance.

According to a further embodiment of the present invention, the gas sensor encompasses a memory. The memory is designed to store a correlation or correspondence between predetermined gases and conductivities as well as an impedance or capacitance. The evaluation device can be designed to identify a gas using the stored correlations between gas and conductivity, and gas and impedance or capacitance. A gas that is to be detected can thereby be inferred particularly easily from an ascertained conductivity and capacitance or impedance.

The above embodiments and refinements in accordance with the present invention can be combined with one another in any way to the extent that is useful. Further possible embodiments, refinements, and implementations of the invention encompass combinations, including ones not explicitly recited, of features of the present invention that are described above or hereinafter with reference to the exemplifying embodiments. In particular, one skilled in the art will also add individual aspects as improvements or supplements to the respective basic form of the present invention.

BRIEF DESCRIPTION OF THE DRAWINGS

The present invention will be explained in more detail below with reference to the exemplifying embodiments shown in the figures.

DETAILED DESCRIPTION OF EXAMPLE EMBODIMENTS

Figure 1:
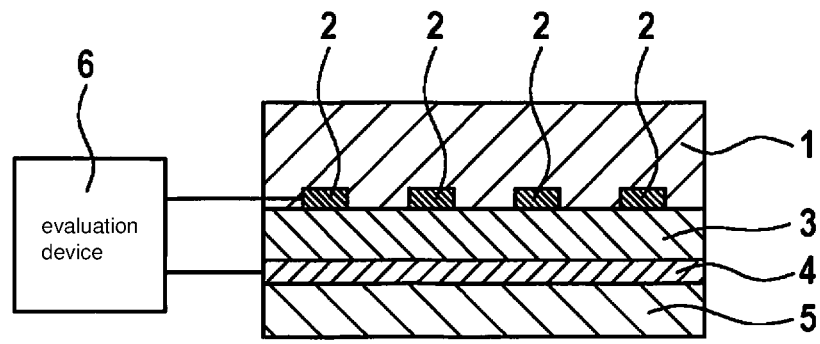
FIG. 1 schematically depicts a cross section through a gas sensor in accordance with an embodiment.

In all the Figures, identical or functionally identical elements and apparatuses are labeled with identical reference characters unless otherwise indicated.

FIG. 1 schematically depicts a cross section through a gas sensor in accordance with an embodiment. The gas sensor encompasses a multi-layer construction. As depicted in FIG. 1, the gas sensor can be disposed on a carrier substrate 5. The following elements are disposed, in ascending order upward, on this carrier substrate 5: Firstly, a back electrode 4 is disposed on carrier substrate 5. A dielectric layer 3 is disposed on back electrode 4, and a front electrode 2 on dielectric layer 3. Front electrode 2 is covered with a gas-sensitive layer 1. Gas-sensitive layer 1 can furthermore also extend into the interstices of front electrode 2 as far as dielectric layer 3. In a further embodiment, gas-sensitive layer 1 can also be disposed only between individual or all elements of front electrode 2. It is furthermore possible to use, for the filling between the elements of front electrode 2, different substances for gas-sensitive layer 1 whose physical and/or chemical properties react to different gases.

Front electrode 2 and back electrode 4 can be electrically coupled to an evaluation device 6 for evaluation and for detection of a gas.

Back electrode 4 can be constituted, for example, from a metal or an organic, electrically conductive material, for instance a substance from the class of the phthalocyanines. Back electrode 4 can furthermore encompass, for example, platinum (Pt), palladium (Pd), gold (Au), rhodium (Rh), rhenium (Re), ruthenium (Ru), indium (In), titanium (Ti), titanium nitride (TiN), tantalum nitride (TaN), or alloys of one or several of those components. Back electrode 4 can furthermore also, for example, be constituted from a semiconductor material, for instance silicon (Si), germanium (Ge), gallium arsenide (GaAs), indium phosphide (InP), silicon carbide (SiC), gallium nitride (GaN), or other semiconductors.

A dielectric or electrically insulating layer is disposed above this back electrode 4. This dielectric layer can be constituted from a known electrically insulating material. Non-limiting examples of the materials of such a dielectric layer 3 are, for instance, oxides, for instance aluminum oxide ($Al_2O_3$) and silicon dioxide ($SiO_2$), or nitrides, for instance silicon nitride ($Si_3N_4$), or the like. The thickness of this dielectric layer 3 can be, for example, up to 10 μm, in particular up to 200 nm. Dielectric layer 3 can furthermore also encompass a ferroelectric, for instance $Bi_{3.15}Sm_{0.85}Ti_3O_{12}$ (BST), lead zirconate titanate (PZT, $Pb(Zr_xTi_{1-x})O_3$), strontium bismuth tantalate (SBT, $SrBi_2Ta_2O_9$), or the like. The thickness of dielectric layer 3 can be in the range around 500 nm or 1 μm.

A front electrode 2 is disposed above this dielectric layer 3. This front electrode 2 has two electrode elements 2-1 and 2-2 electrically separated from one another, as will be explained in further detail in conjunction with FIG. 2. In particular, front electrode 2 can be embodied in the form of an interdigital electrode. An interdigital electrode of this kind has two comb-like electrically conductive structures that engage into one another.

Front electrode 2, having its two electrode elements 2-1 and 2-2, is furthermore covered with a gas-sensitive layer 1. This gas-sensitive layer 1 can involve, for example, organic compounds such as phthalocyanines, metal oxides, and composite materials made up of a conductive electrode and, for instance, carbonates such as barium carbonate.

Figure 2:
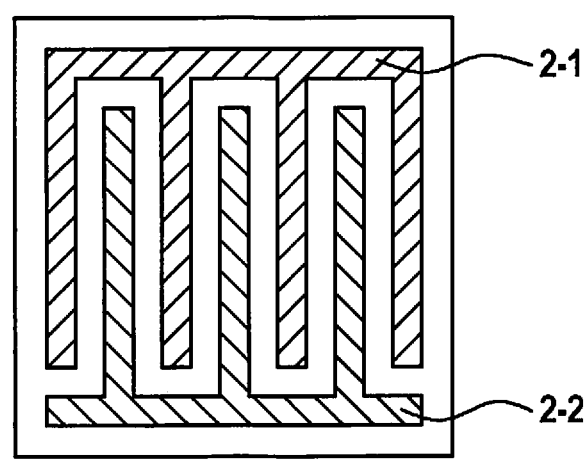
FIG. 2 schematically depicts a plan view of a gas sensor in accordance with an embodiment.

FIG. 2 schematically depicts a plan view of a gas sensor in accordance with an embodiment. The two electrode elements 2-1 and 2-2 of the front electrode, constituting separate electrically conductive structures, are visible in particular. The two electrode elements 2-1 and 2-2 of front electrode 2 are electrically separated from one another. The material of gas-sensitive layer 1 is disposed in the interstices between the two electrode elements 2-1 and 2-2 of front electrode 2 and above front electrode 2.

Alternatively, gas-sensitive layer 1 can also be disposed on dielectric layer 3, and electrode elements 2-1 and 2-2 of front electrode 2 can then be deposited or disposed on gas-sensitive layer 1.

The construction of the gas sensor as described thus encompasses a combination of two sensor elements. On the one hand, an electrical conductivity of gas-sensitive layer 1 can be determined by way of the two electrode elements 2-1 and 2-2 of front electrode 2. For that purpose, an electrical voltage can be applied, for example by evaluation device 6, between the two electrode elements 2-1 and 2-2, and the electrical current established in that context can be measured. The electrical conductivity can thus be calculated from the ratio between the measured electrical current and the applied electrical voltage. If the material of gas-sensitive layer 1 is a material whose conductivity is dependent on a concentration of one or several predetermined gaseous substance, the corresponding concentration, or at least the presence, of a corresponding substance can thus be inferred from the calculation of the electrical conductivity.

The gas sensor described above moreover constitutes a further sensor unit made up of a back electrode 4, dielectric layer 3, and front electrode 2. A capacitance or impedance of the construction made up of back electrode 4, dielectric layer 3, and front electrode 2 can be determined in particular by electrically connecting the two electrode elements 2-1 and 2-2 of front electrode 2. An alternating electrical voltage can be applied for that purpose, for example by evaluation device 6, between back electrode 4 and the short-circuited electrode elements 2-1 and 2-2. The corresponding capacitance or impedance can then be inferred by measuring the alternating electrical current that occurs.

For a gas sensor according to the present invention that combines impedance or capacitance measurement for ascertaining a change in a work function with measurement of a gas-dependent change in electrical conductivity, however, it is necessary not only for the gas being detected to influence gas-sensitive layer 1, but also for the gas being detected to influence dielectric layer 3 by way of its interaction with gas-sensitive layer 1. Gas-sensitive layer 1 can have for that purpose, for example, a porous structure or cavities. Such cavities can be constituted, for example, by the fact that a locally preferred deposition of the material of gas-sensitive layer 1 onto electrode elements 2-1 and 2-2 occurs. This can be achieved in particular by the fact that the material of gas-sensitive layer 1, in particular when it is an organic material, grows preferentially on electrodes 2-1 and 2-2. Cavities by way of which a gas to be detected can interact with dielectric layer 3 located below front electrode 2 thus form above the exposed substrate regions. This effect can be achieved, for example, by additionally coating dielectric layer 3 with a material on which the gas-sensitive layer adheres or grows particularly poorly. Once gas-sensitive layer 1 has grown on the substrate, this additional material can, if applicable, be dissolved out again.

The gas sensor made up of back electrode 4, dielectric layer 3, front electrode 2, and gas-sensitive layer 1 can be disposed, for example, on a substrate 5. In particular, this substrate 5 can encompass, for example, a heating device (not depicted here). The gas sensor can be heated to a desired predetermined temperature by way of such a heating device. Controlled boundary conditions during detection of a gas can thereby be deliberately created. In particular, any moisture that may condense on the gas sensor can be eliminated by heating the gas sensor.

For qualitative or quantitative detection of a gas, firstly an electrical conductivity between the two electrode elements 2-1 and 2-2 of front electrode 2 can therefore be determined, and furthermore the capacitance or impedance between front electrode 2 and back electrode 4 can be ascertained. Preferably the electrical conductivity is determined, and the capacitance or impedance ascertained, immediately sequentially. Alternatively, a simultaneous measurement of the electrical conductivity and the capacitance or impedance is possible. A simultaneous measurement is conceivable in particular when the potential differences between electrode elements 2-1 and 2-2 of front electrode 2 are small as compared with a potential difference between front electrode 2 and gas-sensitive layer 1. Qualitative and/or quantitative detection of a gas can then be accomplished based on these two measurements, i.e. based on the ascertained conductivity and additionally based on the ascertained capacitance or impedance. For that purpose, for example, evaluation device 6 can compare the ascertained conductivity and the ascertained capacitance or impedance with values previously stored in a memory, and from that can detect the presence of a predetermined gas or determine the concentration of a predetermined gaseous substance.

Once an above-described measurement has been accomplished by combining a conductivity measurement and a capacitance or impedance measurement, the next measurement can be accomplished immediately. Alternatively, it is also possible firstly for a predetermined idle time to occur after such a measurement. Neither a conductivity measurement nor a measurement of capacitance or impedance is performed during this idle time. In addition, possible heating of the gas sensor can also, if applicable, be deactivated or at least decreased during this idle time. It is thereby possible to reduce the amount of energy required.

It is moreover also possible for only the measurement by way of a sensor portion of the gas sensor to be accomplished, continuously or periodically at predetermined time intervals. For example, only the measurement of electrical conductivity can be performed. Alternatively, only the measurement of impedance or capacitance can also be performed. Only if a significant change occurs during measurement by way of one measurement principle can the respective further measurement method additionally be applied for further support or for verification of the ascertained values.

Figure 3:
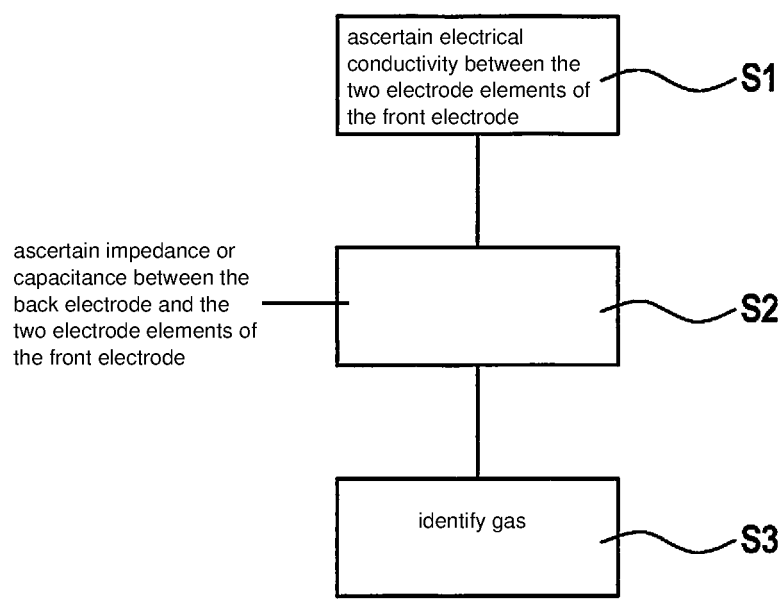
FIG. 3 schematically depicts a flow chart that is the basis of a method according to an embodiment of the present invention.

FIG. 3 schematically depicts a flow chart that is the basis of a method for detecting a gas using a gas sensor according to the present invention. In step S1, firstly an electrical conductivity between the two electrode elements 2-1 and 2-2 of front electrode 2 is ascertained. In step S2 an impedance or a capacitance between back electrode 4 and the two electrode elements 2-1 and 2-2 of front electrode 2 is furthermore ascertained. In step S3 a gas is then identified. The identification of this gas is accomplished, for example, based on a comparison of predetermined values with the ascertained values of the electrical conductivity between the two electrode elements 2-1 and 2-2 of the front electrode 2, and the ascertained impedance or capacitance between back electrode 4 and the two electrode elements 2-1, 2-2 of front electrode 2.

As already indicated previously, the next measurement can be effected immediately by ascertaining the electrical conductivity and the impedance or capacitance. Alternatively, after a successful measurement it is also possible to apply a delay time during which neither electrical conductivity nor impedance or capacitance is measured.

In summary, the present invention relates to a gas sensor. The gas sensor according to the present invention combines two separate measurement methods in one common configuration. In particular, by way of the gas sensor according to the present invention a qualitative or quantitative measurement of gases can be carried out based on measurement of a variation in electrical conductivity and measurement of a change in work function based on a variation in the capacitance or impedance between two electrodes.

What is claimed is:
1. A gas sensor, comprising:
   an electrically conductive back electrode;
   a front electrode having two electrode elements electrically separated from one another;

a dielectric layer that is disposed between the back electrode and the front electrode;

a gas-sensitive layer that is disposed on a side of the dielectric layer on which the front electrode is disposed, and an evaluation device that is electrically coupled to the back electrode and to the two electrode elements of the front electrode and is configured to ascertain an electrical conductivity between the two electrode elements of the front electrode.

2. The gas sensor as recited in claim 1, wherein the gas-sensitive layer encompasses phthalocyanine, a metal oxide, and/or a carbonate.

3. The gas sensor as recited in claim 1, wherein the dielectric layer encompasses a ferroelectric.

4. The gas sensor as recited in claim 1, wherein the gas-sensitive layer encompasses a porous structure and/or cavities.

5. The gas sensor as recited in claim 1, wherein the back electrode is disposed on a carrier substrate.

6. The gas sensor as recited in claim 1, wherein the front electrode encompasses an interdigital electrode.

7. A gas sensor, comprising:

an electrically conductive back electrode;

a front electrode having two electrode elements electrically separated from one another;

a dielectric layer that is disposed between the back electrode and the front electrode;

a gas-sensitive layer that is disposed on a side of the dielectric layer on which the front electrode is disposed; and an evaluation device that is electrically coupled to the back electrode and to the two electrode elements of the front electrode and is configured to ascertain an electrical conductivity between the two electrode elements of the front electrode and is furthermore configured to ascertain an impedance and/or a capacitance between the back electrode and the two electrode elements of the front electrode.

8. The gas sensor as recited in claim 7, wherein the evaluation device is configured to connect the electrode elements of the front electrode electrically to one another when the impedance and/or capacitance between the back electrode and the two electrode elements of the front electrode is being ascertained.

9. A gas sensor, comprising:

an electrically conductive back electrode;

a front electrode having two electrode elements electrically separated from one another;

a dielectric layer that is disposed between the back electrode and the front electrode;

a gas-sensitive layer that is disposed on a side of the dielectric layer on which the front electrode is disposed; and a memory storing a correlation between predetermined gases and conductivities as well as an impedance and/or capacitance, the evaluation device being configured to identify a gas using the stored correlations between gases and conductivity and impedance and/or capacitance.

10. A method for detecting a gas using a gas sensor, the gas sensor including an electrically conductive back electrode, a front electrode having two electrode elements electrically separated from one another, a dielectric layer that is disposed between the back electrode and the front electrode, and a gas-sensitive layer that is disposed on a side of the dielectric layer on which the front electrode is disposed, the method comprising:

ascertaining an electrical conductivity between the two electrode elements of the front electrode;

ascertaining an impedance and/or a capacitance between the back electrode and the two electrode elements of the front electrode; and identifying a gas based on a comparison of the ascertained electrical conductivity between the two electrode elements of the front electrode, and of the ascertained impedance and/or capacitance between the back electrode and the two electrode elements of the front electrode, with predetermined values.

* * * * *